US005508197A

United States Patent [19]

Hansen et al.

[11] Patent Number: 5,508,197

[45] Date of Patent: Apr. 16, 1996

[54] HIGH-SPEED THERMAL CYCLING SYSTEM AND METHOD OF USE

[75] Inventors: Anthony D. A. Hansen, Berkely; Joseph M. Jaklevic, Lafayette, both of Calif.

[73] Assignee: The Regents, University of California, Berkeley, Calif.

[21] Appl. No.: 279,412

[22] Filed: Jul. 25, 1994

[51] Int. Cl.[6] .......... C12M 1/36

[52] U.S. Cl. .......... 435/285.1; 435/809; 435/286.1; 935/88; 422/109; 422/110; 422/115; 422/116

[58] Field of Search .......... 435/289, 290, 435/316, 809; 935/88; 422/109, 110, 115, 116

[56] References Cited

U.S. PATENT DOCUMENTS

| | | | |
|---|---|---|---|
| 3,811,842 | 5/1974 | Diebler et al. | 23/259 |
| 5,443,791 | 8/1995 | Cathcart et al. | 422/65 |

*Primary Examiner*—David A. Redding

*Attorney, Agent, or Firm*—Pepi Ross; Paul R. Martin

[57] ABSTRACT

A thermal cycling system and method of use are described. The thermal cycling system is based on the-circulation of temperature-controlled water directly to the underside of thin-walled polycarbonate microtiter plates. The water flow is selected from a manifold fed by pumps from heated reservoirs. The plate wells are loaded with typically 15–20 μl of reagent mix for the PCR process. Heat transfer through the thin polycarbonate is sufficiently rapid that the contents reach thermal equilibrium with the water in less than 15 seconds. Complete PCR amplification runs of 40 three-step cycles have been performed in as little as 14.5 minutes, with the results showing substantially enhanced specificity compared to conventional technology requiring run times in excess of 100 minutes. The plate clamping station is designed to be amenable to robotic loading and unloading of the system. It includes a heated lid, thus eliminating the need for mineral oil overlay of the reactants. The present system includes three or more plate holder stations, fed from common reservoirs but operating with independent switching cycles. The system can be modularly expanded.

23 Claims, 6 Drawing Sheets

HIGH-SPEED THERMAL CYCLING SYSTEM AND METHOD OF USE

STATEMENT OF GOVERNMENT RIGHTS

This invention was made with Government support under Contract No. DE-AC03-76SF00098 between the U.S. Department of Energy and the University of California for the operation of Lawrence Berkeley Laboratory. The Government has certain rights in this invention.

BACKGROUND OF THE INVENTION

The present invention generally relates to the field of bio-technology, genetic research, and DNA diagnostics, and it more specifically relates to an automated high speed thermal cycling system for carrying out temperature controlled processes, including but not limited to polymerase chain reactions for identifying and amplifying specific elements of a genetic sequence in a sample of material.

A rapidly growing technique being employed by many molecular biology laboratories is the amplification of DNA sequences through polymerase chain reaction (PCR), a technique which utilizes thermal cycling systems. The PCR process was introduced in the 1980's and has revolutionized genetics-related research. PCR replicates a small amount of DNA in a series of heating and cooling cycles, and has been used in diverse research applications, including molecular biology DNA sequencing, cloning, research into mutagenesis and gene synthesis using published DNA sequences.

Generally, thermal cyclers allow the PCR process to proceed automatically by subjecting the reagents-DNA nucleotides and a heat-tolerant polymerase, among others, to a user-specified heating and cooling sequence. Research analyses usually require many copies of a particular targeted DNA segment. PCR is a relatively quick and highly efficient way to copy or amplify DNA molecules in a test tube without needing cell cultures. PCR allows researchers to amplify any DNA sequence regardless of its origin (i.e., virus, bacteria, plant, or any human cell) hundreds of millions of times in a matter of hours.

PCR is especially valuable because the reaction can amplify extremely small amounts of starting material. Thus, it has had a major impact on clinical medicine, genetic research and diagnosis, and evolutionary biology as well as forensic science, and has allowed a spectrum of advances ranging from the identification of novel genes and pathogens to the quantization of characterized nucleotide sequences.

The PCR process is based on a special polymerase enzyme (a protein acting as a catalyst) that catalyzes the synthesis of a new strand of DNA complementary to an existing target strand. The starting mixture contains the DNA sample of interest, the four building blocks of DNA (called DNA bases), and two DNA fragments (called primers) that flank the target sequence.

A single PCR cycle includes three steps: denaturation, primer binding or annealing, and DNA synthesis or extending. During denaturation, the starting mixture is first heated to about 94° C. to 96° C. for separating the double strands of DNA. After denaturation of the DNA, the mixture is cooled to about 55° C. to allow the primers to bind to their complementary sequences on the separated strands. The primers define the ends of the DNA to be duplicated. Then, the mixture is heated to a temperature of about 72° C., so that the DNA polymerase catalyzes the extension of the annealed primers on the template strand.

Repeated cycles of denaturation, primer annealing, and primer extension result in the exponential multiplication of the target DNA because each new double strand separates to become two new DNA templates for further synthesis. Some 20 cycles of the PCR can amplify the target DNA by a factor of a million in about one to two hours.

A typical instrument for automating PCR comprises a temperature-controlled sample block having a plurality of wells. A block may have, for example, 96 such wells in an 8×12 format. Each well receives a thin-walled reaction tube having a volume accommodating samples in the range of 10 to 100 μl. Nucleic acids and reagents are placed within these tubes which are then placed into the wells, in the temperature-controlled sample block. The system is then cycled through a heating and cooling sequence for achieving the desired DNA amplification.

It is important that thermal cyclers reach appropriate temperatures quickly and provide a uniform temperature over all the samples, to ensure accurate and uniform results. This is difficult to achieve, and manufacturers of thermal cyclers have turned to different technologies for thermal cycling, i.e., cyclically heating the samples and then cooling them down. Most, but not all, use an electrically heated element to deliver heat to a metal plate that surrounds the sample tubes. The heating cycle of such an element is relatively long, and its temperature can sometimes exceed a predetermined upper limit.

For cooling, several approaches are used. Some models do not offer active control when it comes to cooling, they simply let excess heat escape into the ambient air. These are the least expensive instruments to manufacture, but they can have uniformity problems. Another method of cooling is that used by Perkin-Elmer, one of the largest manufacturers of thermal cyclers. This approach relies on vapor compression heat pumping, which is similar to a typical refrigeration unit. Other devices cool the samples using running water which is then discarded. However, these devices consume an extensive amount of energy, and are not energy efficient.

Another technology used in thermal cyclers is an electronic process called the Peltier effect. Depending on the direction of the electrical current in a Peltier unit, which includes two ceramic outer layers sandwiching an inner layer of semiconductor material, it can actively cool one surface while heating the other. This effect can cause a temperature differential between the surfaces. Reversing the flow of the current reverses the flow of heat, but the cooling capacity of these units is limited.

Conventional thermal cyclers suffer from drawbacks and inaccuracies, among which are the following: In most of these thermal cyclers heat transfer to the reagents contained in the tubes is slow, and the overall cycling time is relatively long, such as 2 hours for the entire amplification run. Furthermore, the biological reagents are subjected to substantial periods of time at intermediate non-ideal temperatures, allowing undesirable reactions to occur. Under these conditions, and depending on the primers used, there can be nonspecific priming, resulting in the amplification of undesired DNA. Research studies have shown that this undesired "background" can be decreased by increasing the rapidity and accuracy of the thermal cycling.

Therefore, it would be desirable to have a new thermal cycling system for effective use in various applications and temperature controlled processes, including but not limited to polymerase chain reactions. This new thermal cycling system should contain samples in the form of small volumes of liquid, typically between 10 and 50 μl. It should automatically and simultaneously process a large number of samples.

The new thermal cycling system should maintain precise control of the temperature cycle. In particular the reagent temperatures must not exceed the highest reaction temperature (i.e., 96° C.), otherwise, the PCR enzyme is rapidly destroyed. The new cycling system should allow a rapid and almost instantaneous change of temperatures between the three steps of each single PCR cycle: denaturing (about 94° C.), annealing (about 55° C.), and extending ( about 72° C.), in order to minimize non-specific binding, i.e., incomplete identification, which may occur at intermediate temperatures.

SUMMARY OF THE INVENTION

Accordingly, it is an object of the present invention to provide a new energy efficient thermal cycling system which addresses the problems presented by conventional thermal cycling systems, and which provides adequate solutions thereto.

It is another object of the present invention to provide a new thermal cycling system for effective use in various applications and temperature controlled processes, including but not limited to polymerase chain reactions.

It is yet another object of the present invention to provide a new thermal cycling system which is capable of automatically and simultaneously varying the temperature of a large number of samples in the form of small volumes of liquid, typically between 10 and 50 microliters.

It is a further object of the present invention to provide a new thermal cycling system which maintains the temperature cycle precisely controlled, and which, in particular, does not allow the upper temperature to exceed a predetermined level.

It is still another object of the present invention to provide a new thermal cycling system which allows a rapid and almost instantaneous change of temperatures between the three steps of each single PCR cycle: denaturing (about 94° C.), annealing (about 55° C.), and extending (about 72° C.), in order to minimize the occurrence of non-specific binding at intermediate temperatures.

Briefly, the above and further objects and advantages of the present invention are realized by a new thermal cycling system and method of use. In the preferred embodiment, this thermal cycling system is based on the circulation of temperature-controlled working fluid directly to the underside of thin-walled polycarbonate microtiter plates. The working fluid flow is selected from a manifold fed by pumps from three heated reservoirs. The plate wells are loaded with typically 15–20 μl of reagent mix for the PCR process. Heat transfer through the thin polycarbonate is sufficiently rapid that the contents reach thermal equilibrium with the working fluid in less than 15 seconds. Multi-well plates in 96-, 192- and 384-well formats can be used. The plate clamping station is designed to be amenable to robotic loading and unloading of the machine. It includes a heated lid, thus eliminating the need for mineral oil overlay of the reactants, which would otherwise be required to prevent evaporation of the sample. The present system has three or more plate holder stations, fed from common reservoirs but operating with independent switching cycles. The system can be modularly expanded.

Some of the potential applications for the inventive thermal cycling system include: (1) Diagnostic use in hospitals and laboratories, such as for identifying specific genetic characteristics in a sample from a patient; (2) biotechnology research, such as for the development of new drugs, identification of desirable genetic characteristics of crops, etc.; (3) biotechnology industry wide applications; and (4) scientific research and development efforts.

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION OF THE PREFERRED EMBODIMENTS

Figure 1:
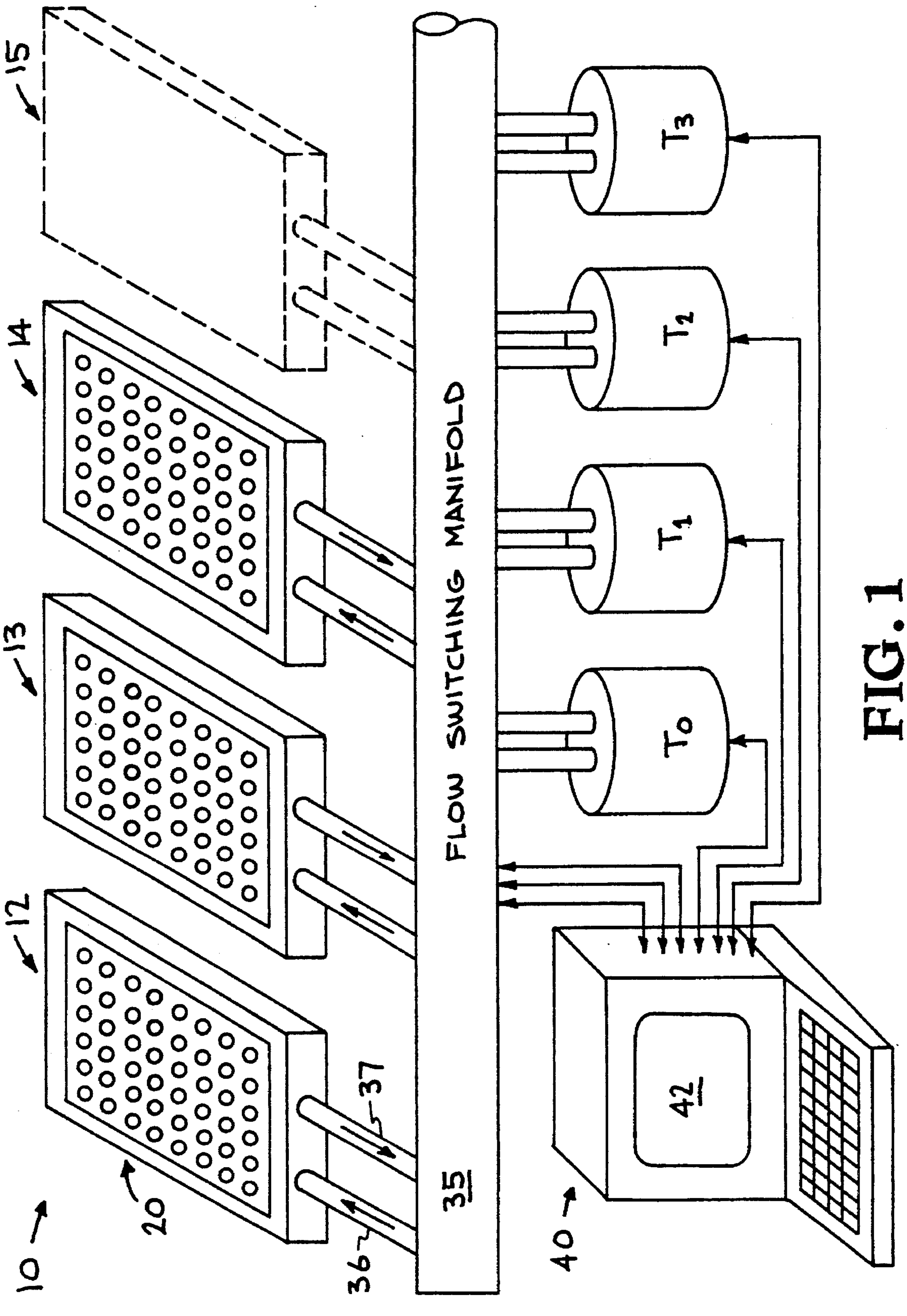
FIG. 1 is a diagrammatic illustration of a thermal cycling system according to the present invention.

Referring now to the drawings, and more particularly to FIG. 1 thereof, there is illustrated a thermal cycling system 10 according to the present invention. The thermal cycling system 10 generally includes a plurality of plate holder stations, such as the stations 12, 13, 14 and 15. These stations can be modularly added or removed from the thermal cycling system 10. Optionally, selected ones of these stations can be operated simultaneously. While only four stations 12, 13, 14 and 15 are shown for illustration purpose, it should be understood that a different number of stations can alternatively be selected.

Figure 2:
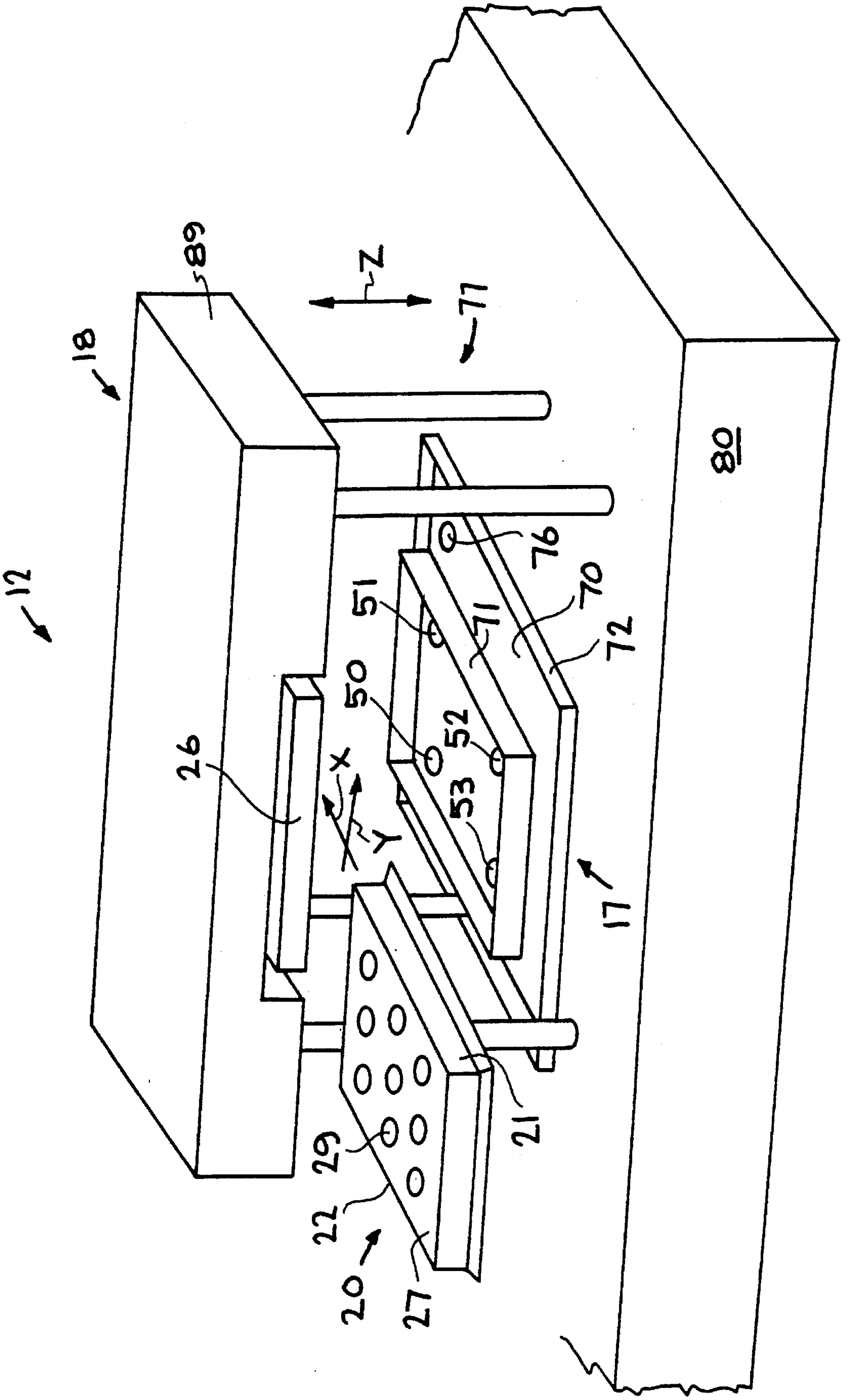
FIG. 2 is a perspective view of a plate holder station forming part of the thermal cycling system of FIG. 1.

FIG. 2 illustrates an exemplary plate holder station 12 in more detail. The plate holder station 12 includes a plate holder or base 17 and a pneumatically operated lid mechanism 18 capable of moving vertically along the Z-direction. The plate holder 17 is specifically shaped and designed to support and retain a microtiter plate 20 during the thermal cycling process.

In operation, the microtiter plate 20 containing the reagents in question is placed onto the plate holder 17, either manually or robotically. For this purpose, the lid mechanism 18 is elevated above the plate holder 17, such that a sufficient clearance is formed therebetween. An operator or a robotic arm (not shown) can hold the microtiter plate 20 by its two opposite sides 21, 22 and simply slide it, first along the X-Y directions within the clearance to position the microtiter plate 20 above the plate holder 17, and thereafter move the microtiter plate 20 downwardly, along the Z-direction. The microtiter plate 20 fits on the plate holder 17 and is securely held in position thereby.

Figure 4:
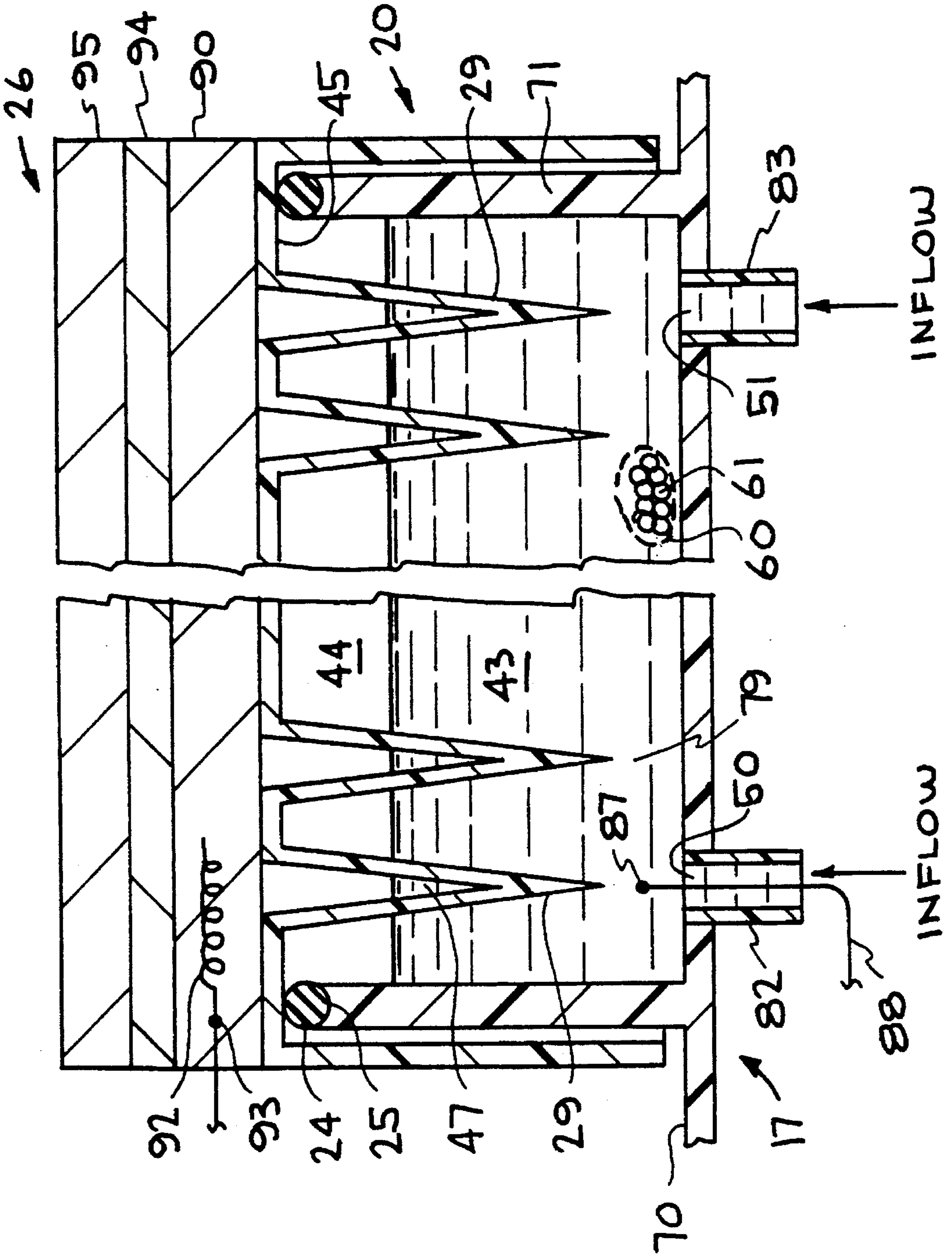
FIG. 4 is a side elevational cross-sectional view of the plate holder of FIG. 3A, taken along line 4—4 thereof, and further illustrating a microtitter plate engaging the plate holder and a lid pressing the microtitter plate in tight engagement with the plate holder.

Under automatic control, the lid mechanism 18 descends on the microtiter plate 20 and the plate holder 17, and exerts a clamping force on top of the microtiter plate 20, to effect a liquid-tight seal provided by an O-ring 24 around the upper lip periphery 25 of the plate holder 17, as further illustrated in FIG. 4. The lid mechanism 18 includes a lid 26 which, in turn, includes a monostatically heated element to maintain the upper surface 27 of the microtiter plate 20 at a preselected constant elevated temperature, thereby reducing evaporative refluxing or distillation of the content of the wells 29 of the microtiter plate 20.

The thermal cycling system 10 further includes a flow switching manifold 35 (FIG. 1) which is comprised of a plumbing system and a plurality of remotely operable valves. The flow switching manifold 35 is fluidly connected to each of the plate holder stations 12–15 via a plurality of plumbing feed lines, such as an inflow conduit (i.e., 36) and an outflow conduit (i.e., 37), for rapidly, selectively and sequentially feeding each of these plate holder stations, independently, with fluids at different temperatures from four temperature controlled reservoirs $T_0$, $T_1$, $T_2$ and $T_3$. Thus, one important feature of the present invention is the rapid switching of the working fluid flow to and from the plate holder stations 12–15.

A computer 40 also forms part of the thermal cycling system 10, and provides a simple operator interface mechanism. Its graphic display 42, which can be a full screen monitor rather than a multi-line LCD display, provides for ease of establishing timing protocols, monitoring temperature changes, and saving all parameters for rapid recall for future operations. Signals from the computer 40 control and regulate the heating of the reservoirs $T_0$, $T_1$, $T_2$ and $T_3$, the operation of the flow switching manifold 35, and the clamping of the heated lid 26. The computer 40 measures the temperatures both in the reservoirs $T_0$, $T_1$, $T_2$ and $T_3$, and of the liquid flow delivered to each plate holder stations 12–15. Internal diagnostic checks alert the operators to any malfunction or out of range temperatures. Additionally, the computer 40 can control the robotic or automatic operation, including the loading and unloading of the microtiter plates, i.e., 20, onto the corresponding plate holders, i.e., 17.

Briefly, under the automatic control of the computer 40, the valves in the flow switching manifold 35 are selectively opened and closed in such a manner as to admit fluid 43 from the temperature controlled reservoirs $T_0$, $T_1$, $T_2$ and $T_3$, via the connecting plumbing, to a cavity 44, as illustrated in FIG. 4. The cavity 44 is defined by the space between the underside 45 of the microtiter plate 20 and the plate holder 17.

Fluid 43 flows at a predetermined relatively high rate within and through the cavity 44, underneath the microtiter plate 20, and causes a turbulent flow, so that the temperature of the fluid 43 within the cavity 44 is evenly distributed, in order for all the wells 29 of each microtiter plate 20 to be uniformly heated. For this purpose, the wells 29 are immersed in the fluid 43, such that the reagents 47 contained therein are completely submerged, to enable a rapid exchange of heat, and thus a rapid change of temperature of the reagent 47.

In order to maintain an even and turbulent flow underneath the microtiter plate 20, the plate holder 17 includes several inlet and outlet openings to allow the fluid to flow in and out of the cavity 44. While FIGS. 1, 3 and 4 illustrate four such openings 50, 51, 52 and 53, it should be understood that a different number of openings can alternatively be selected.

When four openings 50–53 are used, the fluid is admitted through two inlet openings 50, 51, and then discharged through two outlet openings 52, 53. The fluid flow rate or velocity is sufficiently high to sweep away, or prevent the formation of any bubbles that may tend to form underneath the microtiter plate 20. Also, the relation between the connections of fluid supply and return from the various reservoirs and pumps within the manifold 35 is such that the direction of the fluid flow underneath the plate 20 reverses its direction for successive portions of the cycle provided by the thermal cycling system 10. This minimizes the buildup of bubbles underneath the plate. At a low flow rate, or with unidirectional flow, air may be trapped in the cavity 44, and thermal contact will not be optimal. The flow rate is preferably at least 10 liters per minute, such that the fluid exchange rate (i.e., renewal underneath the microtiter plate 20) is several times per second. Since the reagent 47 is contained in a thin-walled well 29, it is possible to exchange heat very rapidly between the reagent 47 and the fluid 43 within the cavity 44, thus leading to a corresponding desirable change of the temperature surrounding the wells 29 and their content.

In the preferred embodiment, the fluid 43 is water. The large thermal capacity of the flowing water (or another heat transfer liquid medium) provides a large thermal reservoir from which the flow of heat is derived. Upon exiting the plate holder stations 12–15, the fluid 43 returns to a specific reservoir through the flow switching manifold 35.

The reservoirs $T_0$, $T_1$, $T_2$ and $T_3$ provide a supply of fluid, i.e., water 43, at closely controlled temperatures, which are monitored by the computer 40. Heat is supplied to the reservoirs $T_0$, $T_1$, $T_2$ and $T_3$ by means of electrical heating elements. The power to these heating elements is controlled to achieve the desired temperatures. Pumps deliver fluid 43 from the reservoirs or reservoir tanks to the various elements of the flow switching manifold 35 by means of suitable plumbing.

Each one of the reservoirs $T_0$, $T_1$, $T_2$ and $T_3$ comprises a closed plumbing loop, such that the fluid leaving the plate holder station 12–15 is returned to the same reservoir from the whence it originated. The plate holder stations 12–15 have a low thermal mass, for minimizing the change in temperature of the fluid 43. One reservoir or set of reservoirs can provide temperature controlled flow to several plate holders stations. For example, in the PCR process, the three reservoirs $T_1$, $T_2$ and $T_3$ are maintained at about 94° C. (for the denaturing step); 55° C. (for the annealing step); and 72°

C. (for the extending step). The fourth reservoir $T_0$ is maintained at a cooler temperature, for example around 4° C., for use at the completion of the PCR cycling process to preserve the reaction products in a stable state until the operator removes the plate. It should be understood to those skilled in the art that while the foregoing temperatures are given for illustrating the PCR process, other temperatures can alternatively be selected when the present thermal cycling system 10 is used for other applications.

While the present thermal cycling system 10 will be described relative to a PCR process, the scope of the invention is not limited to PCR processes. The rapid change of temperatures either cyclical or one change at a time can be used to minimize the time at which reactions occur, and for better specificity. Other chemical, biochemical or biotechnology processes where different temperatures are needed, are amenable to be used with the present thermal cycling system 10.

The thermal cycling system 10 according to the present invention has been experimentally tested based on the circulation of temperature-controlled water directly to the underside of thin-walled polycarbonate microtiter plates. The water flow is selected from a manifold fed by pumps from three heated reservoirs. The plate wells are loaded with typically 15–20 µl of reagent mix for the PCR process. Heat transfer through the thin polycarbonate is sufficiently rapid that the contents reach thermal equilibrium with the water in less than 15 seconds, and improvements in performance are even observed in non-equilibrium runs in which the temperature switching is more rapid. Complete PCR amplification runs of 40 three-step cycles have been performed in as little as 14.5 minutes, with the results showing substantially enhanced specificity compared to conventional technology requiring run times in excess of 100 minutes. A variety of microtiter plates, such as 96-, 192- and 384-well plates can be used. The enhanced performance and specificity observed in some cases may allow for extension of PCR methods in mapping and sequencing strategies to situations in which conventional technology does not provide satisfactory results.

In one embodiment, the thermal cycling system 10 includes three plate stations, fed from common reservoirs but operating with independent switching cycles, with the ability to add more stations modularly. The three-station system may be able to process several thousands of PCR reactions (for example 20,000 reactions) per 8-hour shift when using 384-well plates. If loaded and unloaded automatically by a robot server, as much as 300,000 PCR reactions could be run in five days.

The computer 40 includes a visual operating interface or display 42, such that intuitive screens show the status of each run. A tabular format assembles and combines the parameters for the run. Protocols may be created, edited, saved and recalled for one station, without interrupting the running of other stations. The computer 40 can be connected to a computer network for integration into a broader instrumentation system. A permanent history file records all activity, and an adhesive label is printed at the end of each run for laboratory notebooks.

Having briefly described some of the main components of the thermal cycling system 10, the following description will provide additional details about the system 10.

Starting with the plate holder stations 12–15, the microtiter plate 17 is commercially available, and includes several wells, for instance 96 wells. A microtiter plate 17 of a higher or lower density of wells can also be used. The microtiter plate 17 has a typical thickness which ranges between 10 and 20 mils. It should be clear that the present invention is adaptable to accommodate pre-formed thin-walled multi-well plates having various configurations or geometries.

In another embodiment of the present invention, individually sealed tubes, vials or other containers can be inserted inside the wells 29. In yet another embodiment of the present invention, pills or capsules, such as the capsule 60 shown in a dotted line in FIG. 4, with the reagent 61 pre-encapsulated therein, are deposited in the cavity 44, and then retrieved at the conclusion of the thermal cycling process. The latter process can be adapted as a drug manufacturing technique, where the individual identity of the capsules or reagents is not important.

Considering now the plate holder 17 in greater detail with respect to FIGS. 1 through 4, it is preferably machined from a single block of low thermal mass material, so as to minimize heat transfer between the plate holder 17 and the fluid during thermal cycling. If the block were made of metal, the heat absorption and retention by the metal would limit the switching rate of the temperatures. In the preferred embodiment, the block is machined out of polycarbonate whose heat capacity is small compared to the heat capacity of the flowing liquid medium.

Another important feature of the plate holder 17 is that it provides a sealed cavity 44 on the underside of the microtiter plate 20. The O-ring 24 ensures a liquid tight seal. The proper material for the plate holder 17 should preferably have a low thermal capacity, it should withstand relatively high temperatures in the range of 100° C., and it should have adequate hardness so that the block is capable of precision machining and to provide sufficient mechanical strength to allow for pressure sealing against the lid mechanism 18. Different materials can be selected for different applications. For extremely high temperatures, it would be foreseeable to use ceramics. The plate holder 17 can be primarily cast or machined from a block of solid material.

In the preferred embodiment illustrated in FIGS. 2 through 4, the plate holder 17 includes a generally rectangular tray 70 that is limited by an inner raised partition 71 and a peripheral wall 72. The raised partition 71 is designed in such a way to provide a rectangularly shaped cavity 44, to match the rectangular outline of a typical microtiter plate 17, and to further provide a leakage catchment channel 74. The channel 74 is provided with a 5 degree slope to convey any leaked water to two drain fittings 75, 76.

Figure 3A:
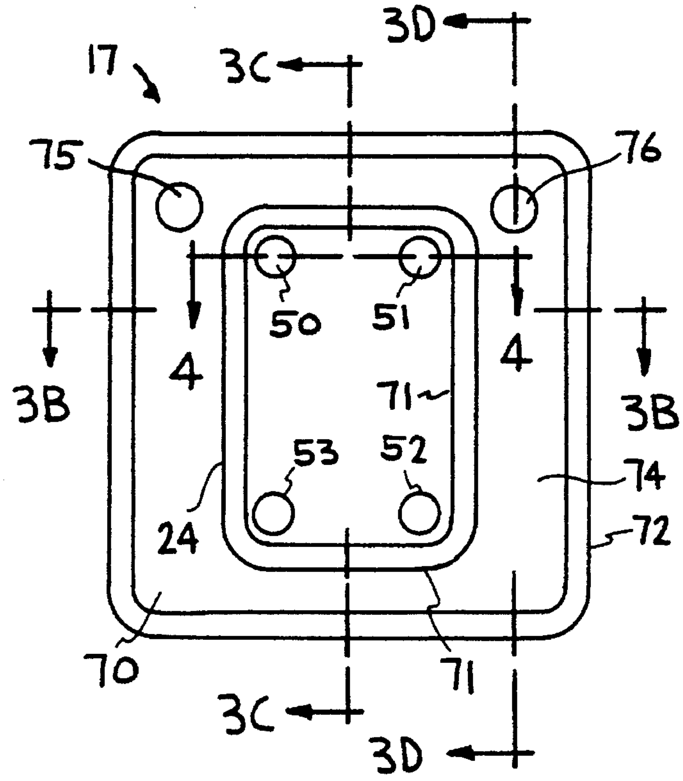
FIG. 3A is a top plan view of a plate holder used in the plate holder station of FIG. 2.
Figure 3B:
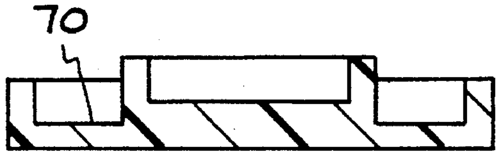
FIG. 3B is a cross-sectional view of the plate holder of FIG. 3A, taken along line B—B thereof.
Figure 3C:
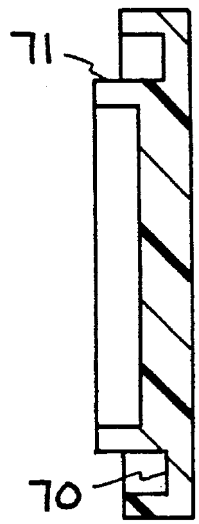
FIG. 3C is a cross-sectional view of the plate holder of FIG. 3A, taken along line C—C thereof.
Figure 3D:
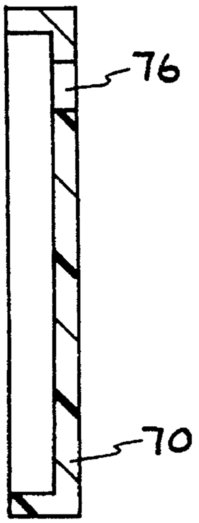
FIG. 3D is a cross-sectional view of the plate holder of FIG. 3A, taken along line D—D thereof.

As illustrated in FIG. 3A, the inlet and outlet openings 50, 51, 52 and 53 are generally located one near each inner corner defined by the tray 70 and the raised partition 71, to insure uniform flow and to eliminate stagnation of the liquid flow. The inner partition 71 includes a groove along its upper peripheral rim for retaining the O-ring 24, in order to provide a liquid-tight seal for the inner cavity 44. The seal is effected by pressure on the lid 26 applied by a pneumatic system 77 (FIG. 1). The inner partition 71 provides adequate mechanical strength to support the sealing pressure, which is about 400 pounds in this example. In the preferred embodiment, the inner partition 71 is about 0.6 inches high, 2.8 inches wide, and 4.15 inches long.

A clearance 79 is formed between the bottom of the wells of the microtiter plate 20 and the plate holder 17. This clearance 79 is minimized in order to optimize the flow stream line through the plate holder 17 and the descending wells 29, and to maximize turbulence. Fluid or water is forced underneath all the wells 29. In the present example, the clearance 79 is about 50 mils.

The plate holder stations 12–15 are robotically amenable by virtue of the fact that the microtiter plate 20 holding the sample or reagent is placed on the plate holder 17 with a simple XYZ movement. The clamping lid mechanism 18 is designed to provide an unrestricted access from one side to facilitate the placement of the microtiter plate 20.

As shown in FIG. 2, the plate holder stations 12–15 are secured on a support structure 80, such as a table top.

Figure 5:
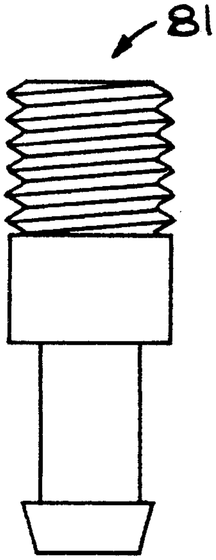
FIG. 5 is a greatly enlarged side elevational view of a tube fitting for engaging the underside of the plate holder of FIGS. 3 and 4.

A plurality of fittings, similar to the fitting 81 shown in FIG. 5 and the fittings 82 and 83 shown in FIG. 4, are tapped and threaded into the openings 50, 51, 52, 53, 75 and 76 of the plate holder 17. These fittings are machined from the same material as the plate holder 17 to eliminate stress fracturing arising from differing thermal expansions during the thermal cycling process. These fittings fluidly connect the plate holder stations 12–15 to the flow switching manifold 35 through the plumbing feed lines 36, 37.

A thermal sensing element 87 (FIG. 4) is introduced into the cavity 44 by means of a catheter 88 through one of the plumbing feed lines, i.e., 36. In another design, one or more thermal sensors can be introduced in the cavity 44 through the inflow and outflow plumbing feed lines. Each thermal sensor 87 reports to the computer 40 the temperature of the fluid delivered to, or discharged from the cavity 44.

In the design of the plate holder stations 12–15, the preferred material can be made in such a way as to be optically clear, thus allowing visual or automatic inspection of the contents of each well 29 during, or at the conclusion of the run. This will allow for the illumination (i.e., laser induced fluorescence) of the reagent by light suitable to influence or catalyze the desired reaction, or to provide a diagnostic readout or analysis at the conclusion of the run. As a result, scanning can be done in situ, and provision is made for routine observation of the liquid flow underneath the microtiter plate 17, to provide a flow visualization, and to check for proper operation by measuring the resulting fluorescence/reflectance. Thus, the present thermal cycling system 10 lends itself to a single step analysis, and provides an optical concept which may be used in diagnostic and quantitative applications.

Referring now more specifically to FIGS. 2 and 4 of the drawings, the lid 26 is supported by a mechanical frame 89 that may be raised or lowered automatically by conventional means such as the pneumatic system 77. When the lid 26 is raised, sufficient clearance is provided for either manual or robotic loading or unloading of the microtiter plates 17. For this purpose, there is provided a completely free access on one side. When the lid 26 is lowered, sufficient force is applied to effect a fluid-tight seal of the microtiter plate 20 against the O-ring 24.

The lid 26 incorporates a heated element as follows: a solid copper block 90 is threaded with a resistance wire 92 and is fitted with a temperature sensor 93. An external controller, such as the computer 40 regulates the power of the resistance wire 92, and thereby maintains the copper block 90 at a substantially constant temperature. The block 90 is supported in an insulating carrier 94, which is inserted in a load bearing frame 95. The underside of the copper block 90 is smooth and applies force to the microtiter plate 20 either with or without the use of a sealing gasket. The outline of the heating block is rectangular, and matches, and is in registration with the pattern of the upper surface of the microtiter plate 20. The thermal cycling system 10 is energy efficient because the working fluid is self-contained and recirculated to the reservoir of its origin.

Figure 6:
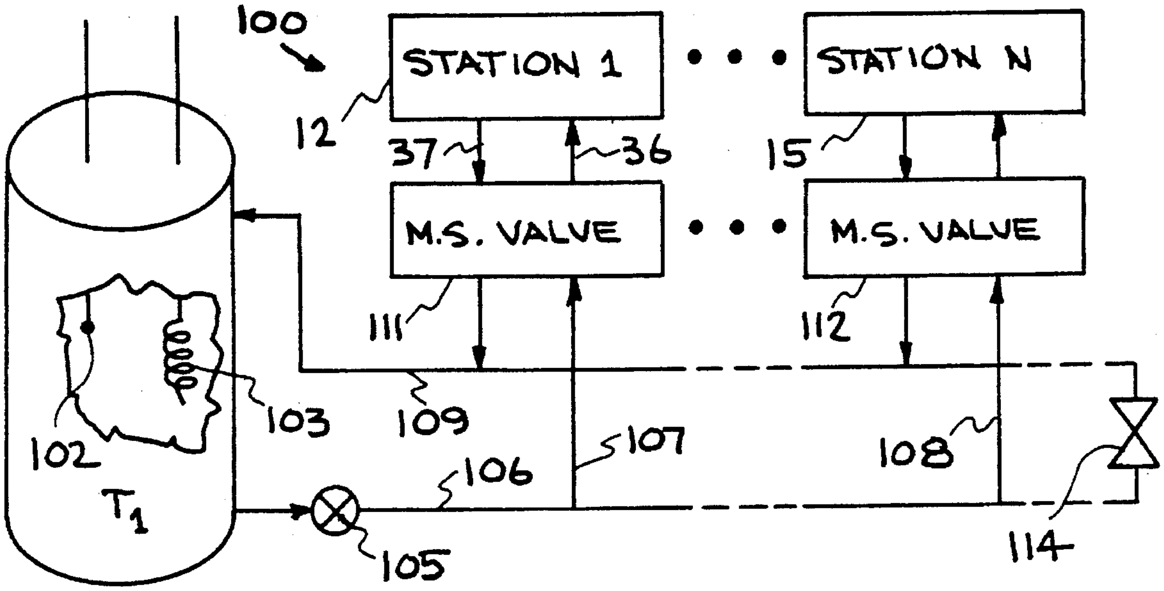
FIG. 6 is a diagrammatic illustration of a reservoir circuit forming part of the thermal cycling system of FIG. 1.

Turning now to FIG. 6, it is a schematic diagram of an exemplary reservoir circuit 100 forming part of the thermal cycling system 10 of FIG. 1. The thermal cycling system 10 preferably includes four such reservoirs circuits, one for each of the reservoirs $T_0$, $T_1$, $T_2$, and $T_3$. The reservoir circuit 100 includes the reservoir tank $T_1$ having an approximate capacity of 25 liters. It should be understood that reservoirs of different capacities can be used.

A temperature sensor 102 measures the temperature of the liquid in the reservoir $T_1$, and a heating element 103 heats up and controls the temperature of the liquid in the reservoir $T_1$, A feed pump 105 draws liquid from the reservoir $T_1$, and supplies it under pressure to the supply side of a manifold pipe 106. Branches from the manifold pipe 106, such as branches 107 and 108 may supply the liquid at the desired temperature to several plate holder stations 12–15, via corresponding manifold switching valves 111 and 112 that are similar in design and function. A return manifold pipe 109 conveys the liquid discharged from the plate holder stations 12–15, via the manifold switching valves 111, 112 back to the reservoir $T_1$ from whence it originated.

In order to avoid stagnation of the liquid flow and resulting cool down, in cases in which none of the plate holder stations 12–15 is in use, a circulation valve 114 is installed at the end of the manifold pipes 106, 109, farthest away from the reservoir $T_1$, This valve 114 is opened automatically to maintain the flow in the manifold pipes 106, 109, and thus to maintain the temperature inside the manifold pipes 106, 109. As a result, provision is made to avoid stagnation and subsequent cooling of the water in the manifold, even for a long run (i.e., the manifold pipes 106, 109 are long). It is therefore one important feature of the present invention to maintain a continuous flow of fluid, sometimes at a very slow rate, within the manifold pipes 106, 109 in order to prevent fluid stagnation and cool down. Provision is also made to automatically fill up the reservoir $T_1$ to compensate for any loss and to provide for overflow of water from the reservoir $T_1$ due to thermal expansion.

The fluid temperature, as determined by the thermal sensor 102 is reported back to the computer 40, which displays a warning message or inhibits the run of that thermal cycling system 10, if conditions are determined to be non-conducive to a successful test, or if the temperature is measured to be outside the specified range. The computer 40 contains a data file of temperature set points in order to accommodate run parameters calling for different temperatures.

Figure 7:
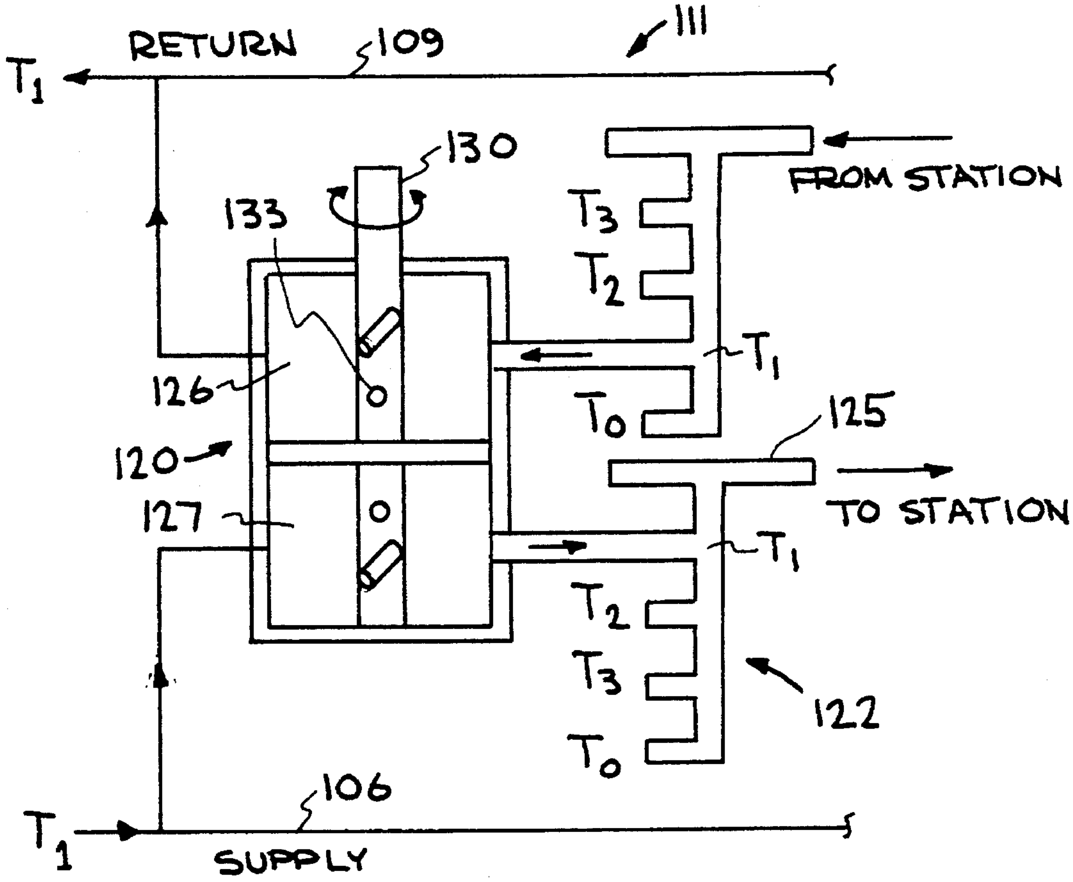
FIG. 7 is a diagrammatic illustration of a manifold switching valve system forming part of the reservoir circuit of FIG. 6.

Referring now to FIG. 7, it illustrates the manifold switching valve 111, which selects a fluid flow from one of several supplies, for example three hot water supplies from reservoirs $T_1$, $T_2$, and $T_3$ and one cold water supply from reservoir $T_0$, and returns the discharged fluid to the same reservoir from whence it originated, after passing through the plate holder stations 12–15. This is achieved by providing each plate holder station 12–15 with a bank of four generally similar rotary valves, exemplified by the rotary valve 120 shown in FIGS. 7, 8(A) and 8(B).

The input to each rotary valve, i.e. , 120 is derived from the four manifold pipes, i.e., 106 in which the temperature controlled fluid flows. The outputs of the four rotary valves are mechanically combined, via a four-way manifold 122, which is connected, via appropriate plumbing 125 to the plate holder stations 12–15. Only one of the four rotary valves (i.e., the rotary valve 120) is opened at any one time in order to select a desired temperature (i.e., $T_1$). The return path mirrors the supply path, so that the discharged fluid is returned to the appropriate reservoir, or in some applications it may be discharged to waste. The operation of the bank of rotary valves is controlled by the computer 40.

Figure 8A:
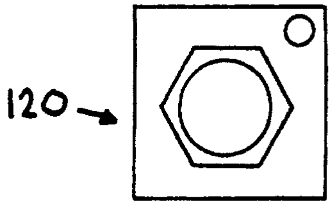
FIG. 8(A) is a top plan view of a rotary valve that has been modified for use as part of the manifold switching valve of FIG. 7.
Figure 8B:
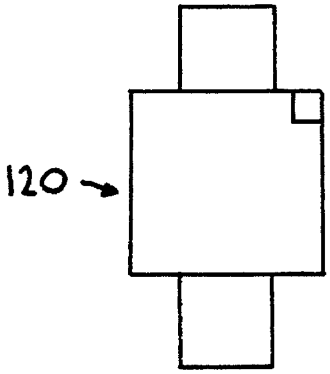
FIG. 8(B) is a side elevational view of the rotary valve of FIG. 8(A)

The rotary valve 120 is illustrated in FIGS. 7, 8(A) and 8(B), and is formed by connecting two rotary plug valves 127, 128 that are mechanically joined so that they rotate in unison. The valves 127, 128 are turned from the OFF position to the ON position by a 90 degrees rotation motion provided by a pneumatic actuator 130 under the control of the computer 40. In the ON position, the two valves 127, 128 offer little resistance to the fluid flow, and permit the full velocity of the fluid flow to be delivered to the plate holder station.

The plug valves 127, 128 are formed by modifying conventional plug valves by the addition of a small diameter internal bypass channel 133, which is illustrated by a broken line in FIG. 7. As a result of this design improvement, a small flow of fluid is continuously maintained through the body of the rotary valve 120 in the OFF position, for maintaining the temperature of the metallic valve bodies at a predetermined level. This feature is important to avoid cool down and undesired low temperature after each switching.

The control computer 40 activates the opening of only one valve according to the desired program. The simultaneous opening of more than one valve is not recommended as it will lead to undesirable mixing of water streams. At the termination of each run, the fourth reservoir $T_0$ supplies cool water (around 4° C.) to cool the sample and to terminate the biological reaction.

All the fluid flow circuits are turned OFF before the lid 26 is raised to retrieve the microtiter plate 17, in order to prevent loss of fluid from the unsealed cavity 44. A pressure interlock of the lid clamping mechanism 18 provides for automatic shut-off of all the liquid streams in the event of loss of clamping pressure, leading to inadequate sealing by the O-ring seal, in order to prevent loss of liquid.

The computer 40 registers all the essential operating temperatures of the thermal cycling system 10. It controls these temperatures by controlling the power supply to various heating elements. It allows the operator to change the reservoir temperature if desired, for a change in protocol. It issues "NOT READY" message when the system is warming up from a cold start. It reports to the operator the accuracy of the delivered temperature during the course of a run. It issues a warning advisory message if the accuracy fails to meet specified temperature norms.

Additionally, the computer 40 continues to lower and raise the lid clamping mechanism 18 by activating a valve admitting compressed air to a pneumatic system. It controls the water flow to the plate holder stations by activating one of the bank of water valves provided for each plate holder station, by allowing a solenoid valve to admit compressed air to a 90 degree-pneumatic actuator linked to the selected liquid valve.

Furthermore, the computer 40 activates the circulation valve 114 at the end of the manifold to maintain flow through the manifold of any liquid flow circuit for which no flow was selected by any plate holder station. It provides an intuitive visual interface for the operator advising the progress of each run and allowing for setting parameters for the run in a tabular and easily understandable format. It provides for operators to add comments and observations, to printout hard copies, to enter annotations for lab notebooks and to communicate over computer networks for integration of the thermal cycling system 10 into a more highly automated operating ensemble.

The computer 40 allows operating protocols to be viewed, revised and easily retrieved by the operators, filed under the operators' names and the nature of the protocol. It provides for interactivity for customization of the mode of operation. It gives flexibility and interactivity with people and other computers and systems.

The configuration of the present thermal cycling system 10 is very flexible, and many stations can be modularly added to a central core including reservoirs, pumps, plumbing, and a central computer. The plate holder stations and the flow switching manifold are modular. The combination of these parts allows the extension of multiple modules without commensurate multiplication of all the components.

Figure 9:
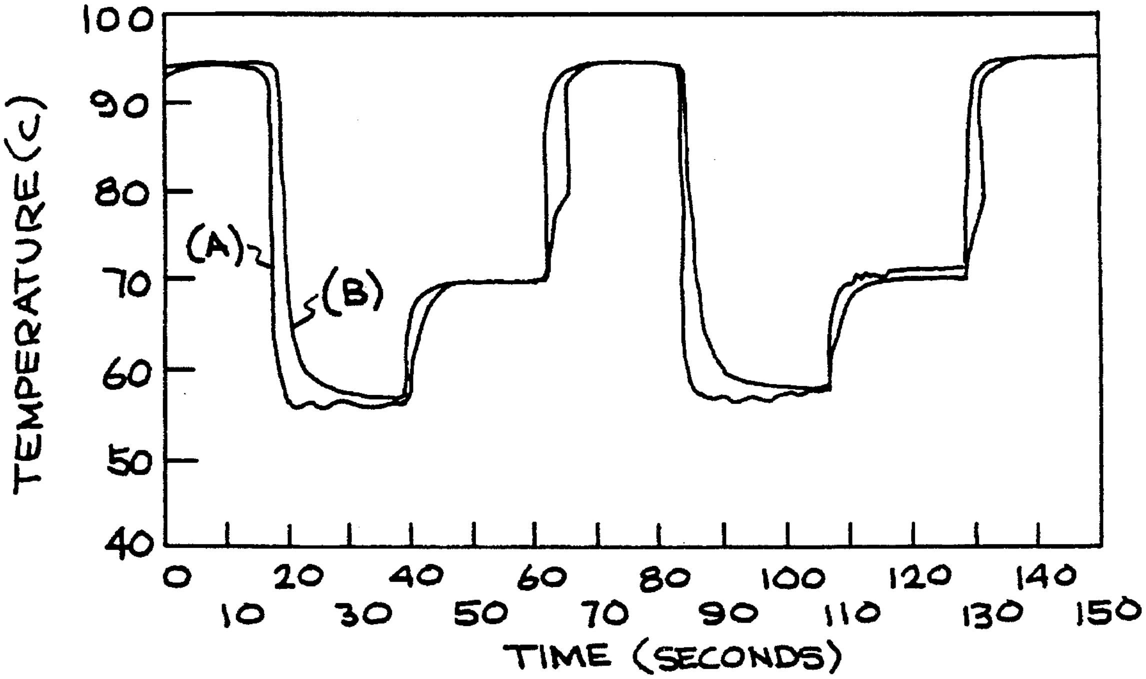
FIG. 9 is a timing chart, illustrating the cyclical temperature response of the working fluid flowing inside the plate holder of FIGS. 3 and 4, and the temperature response of the reagent inside a well of the microtiter plate, obtained by the thermal cycling system of FIG. 1.

FIG. 9 includes two timing charts. The first timing chart (A) illustrates the cyclical temperature response of the fluid delivered to the cavity 44, while the other timing chart illustrates the cyclical temperature response of the sample volume of 15 microliters in the wells 29 of the microtiter plates 20, as determined by a small sensor immersed in a well 29. This data shows that the sample volume equilibrates with the delivered temperature within approximately eight seconds. The time lag of a few seconds reflects the transfer of heat through the thin wall of the microtiter plate 20.

The greatly increased rapidity of the temperature switching is believed to improve the specificity of certain biological reactions and to reduce the background of unwanted products which could have formed if the reagents were maintained at intermediate temperatures for a relatively long period of time.

The foregoing description of the invention has been presented for purposes of illustration and description. It is not intended to be exhaustive or to limit the invention to the precise forms described, and obviously many other modifications am possible in light of the above teaching. The embodiments were chosen in order to explain most clearly the principles of the invention and its practical applications, thereby to enable others in the art to utilize most effectively the invention in various other embodiments and with various other modifications as may be suited to the particular use contemplated.

What is claimed is:

1. A thermal cycling system comprising in combination:

a plurality of plate holder stations, each of which including a plate holder for supporting and engaging a plate during a thermal cycling process, and a lid mechanism for exerting a clamping force on said plate; and a flow switching manifold fluidly connected to each of said plate holder stations for rapidly, selectively and sequentially feeding each of said plate holder stations, independently, with fluids at different temperatures from a plurality of temperature controlled reservoirs.

2. The thermal cycling system according to claim 1, further including a computer system for providing a convenient operator interface mechanism, and for controlling and regulating the heating of said plurality of temperature controlled reservoirs.

3. The thermal cycling system according to claim 2, wherein said lid mechanism includes a lid which, in turn, includes a monostatically heated element to maintain said lid at a preselected constant elevated temperature.

4. The thermal cycling system according to claim 2, wherein when said plate engages said plate holder, a cavity is formed therebetween, underneath said plate;

wherein said flow switching manifold is formed of a plumbing system and a plurality of remotely operable valves; and wherein said remotely operable valves are selectively opened and closed in such a manner as to admit a selected fluid from one of said plurality of temperature controlled reservoirs to said cavity.

5. The thermal cycling system according to claim 4, wherein said selected fluid flows at a predetermined relatively high rate within and through said cavity, and causes a turbulent flow, so that the temperature of said fluid within said cavity is generally evenly distributed, in order for said plate to be uniformly heated.

6. The thermal cycling system according to claim 5, wherein said plate holder includes a plurality of inlet and outlet openings to allow said selected fluid to flow in and out of said cavity.

7. The thermal cycling system according to claim 6, wherein said plate holder includes two inlet and two outlet openings.

8. The thermal cycling system according to claim 7, wherein the flow rate of said selected fluid is sufficiently high to prevent the formation of bubbles that may tend to form inside said cavity.

9. The thermal cycling system according to claim 8, wherein said selected fluid is water.

10. The thermal cycling system according to claim 8, wherein each of said reservoirs include a closed plumbing loop, such that said selected fluid leaving said plate holder station is returned to its reservoir of origin.

11. The thermal cycling system according to claim 10, wherein each of said plate holder stations has a low thermal mass, for minimizing the change in temperature of said selected fluid flowing within said cavity.

12. The thermal cycling system according to claim 11 for use in a PCR cycling process, which includes three reservoirs maintained at three preselected different temperatures.

13. The thermal cycling system according to claim 12, wherein a first one of said temperatures is about 94° C. for a denaturing step;

a second one of said temperatures is about 55° C. for an annealing step; and a third one of said temperatures is about 72° C. for an extending step.

14. The thermal cycling system according to claim 13, further including a fourth reservoir maintained at a cooler temperature for use at the completion of said PCR cycling process.

15. The thermal cycling system according to claim 14, wherein said plate holder is machined from a single block of low thermal mass material, so as to minimize heat transfer between said plate holder and said selected fluid during thermal cycling.

16. The thermal cycling system according to claim 15, wherein said block is made of polycarbonate whose heat capacity is small compared to the heat capacity of the said selected fluid.

17. The thermal cycling system according to claim 16, wherein said plate holder includes a rectangular tray that is limited by an inner raised partition and a peripheral wall; and wherein said raised partition provides a rectangularly shaped cavity for matching the outline of a rectangularly shaped plate, and to further provide a leakage catchment channel.

18. The thermal cycling system according to claim 17, wherein said leakage catchment channel is sloped to convey leaked water to at least one drain fitting.

19. The thermal cycling system according to claim 18, wherein said plate holder includes a plurality of fittings that are machined from the same material as said plate holder, to eliminate stress fracturing arising from differing thermal expansions during said thermal cycling.

20. The thermal cycling system according to claim 2, further including a plurality of reservoir circuits, each of which corresponding to one of said a plurality of temperature controlled reservoirs, wherein each of said reservoir circuits includes a reservoir tank, a temperature sensor for measuring the temperature of a fluid in said reservoir tank, and a heating element for heating and controlling the temperature of said fluid in said reservoir tank.

21. The thermal cycling system according to claim 20, wherein each of said plurality of reservoir circuits further includes a feed pump for drawing said fluid from said reservoir tank, and for supplying it under pressure to a manifold pipe.

22. The thermal cycling system according to claim 21, wherein each of said plurality of reservoir circuits further includes a circulation valve disposed farther away from said reservoir tank in order to avoid stagnation of said fluid and resulting cool down.

23. The thermal cycling system according to claim 22, wherein each of said plurality of reservoir circuits further includes a manifold switching valve for selecting a fluid from one of said plurality of temperature controlled reservoirs, and for returning said selected fluid to its reservoir of origin.

* * * * *